United States Patent [19]

Shimoyama et al.

[11] Patent Number: 5,358,538
[45] Date of Patent: Oct. 25, 1994

[54] PROCESS FOR PRODUCTION OF BLACK COLORING MATERIAL AND COSMETICS CONTAINING SAID BLACK COLORING MATERIAL AND USE THEREOF

[75] Inventors: Susumu Shimoyama, Hasuda; Ujo Maeda; Keiko Maeda, both of Kyoto; Yasuko Noda, Atsugi; Kunio Kataoka, Fuji; Eiichi Eto, Numazu; Satoru Shimoyama; Tasuku Shimoyama, both of Minamiashigara, all of Japan

[73] Assignee: Ihara Chemical Industry Co., Ltd., Tokyo, Japan

[21] Appl. No.: 838,305

[22] PCT Filed: Jul. 10, 1991

[86] PCT No.: PCT/JP91/00921
§ 371 Date: Mar. 10, 1992
§ 102(e) Date: Mar. 10, 1992

[87] PCT Pub. No.: WO92/01022
PCT Pub. Date: Jan. 23, 1992

[30] Foreign Application Priority Data

Jul. 11, 1990 [JP] Japan .................. 2-183537

[51] Int. Cl.$^5$ .............................................. C09B 67/00
[52] U.S. Cl. .......................................... 8/597; 8/516; 8/517; 8/663; 8/580; 8/594; 8/907
[58] Field of Search ............... 8/516, 517, 663, 580, 8/594, 597, 907

[56] References Cited

U.S. PATENT DOCUMENTS 3,311,444 3/1967 Krallman ................. 8/663

FOREIGN PATENT DOCUMENTS 4848649 7/1973 Japan .

OTHER PUBLICATIONS

K. Takagi et al., "Amination of 5,8-Dihydroxy-1,-4-naphthoquinone," Dyes and Pigments, 1984 (U.K.), pp. 241–251.

Primary Examiner—Anthony McFarlane
Assistant Examiner—E. D. Irzinski
Attorney, Agent, or Firm—Davis Hoxie Faithfull & Hapgood

[57] ABSTRACT

A process for the production of a black coloring material characterised by treating a compound selected from finely powdered sugar, protein and a polyamide polymer, having amino groups with a naphthoquinone derivative represented by the general formula (1):

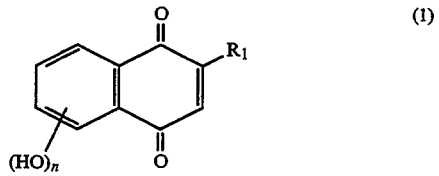

wherein $R_1$ represents a hydrogen atom, a hydroxyl group, a halogen atom, or a group represented by the following formula:

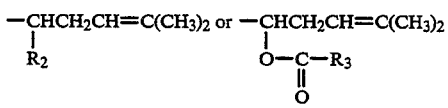

wherein $R_2$ represents a hydrogen atom or a hydroxyl group, $R_3$ represents an alkyl group, an alkenyl group or a hydroxylalkyl group, and n represents 1 or 2; cosmetics comprising a black coloring material produced by the above process; and a process for staining a substrate using the obtained black coloring material.

17 Claims, 15 Drawing Sheets

PROCESS FOR PRODUCTION OF BLACK COLORING MATERIAL AND COSMETICS CONTAINING SAID BLACK COLORING MATERIAL AND USE THEREOF

TECHNICAL FIELD

The present invention relates to a process for the production of a black coloring material, cosmetics using the black coloring material, and a process for staining a fiber black by using the process for the production of the black coloring material.

BACKGROUND ART

As conventional black coloring materials, inorganic pigments such as carbon black and black iron oxide, organic pigments such as aniline black, tar dyestuff such as Black 401, and other various kinds of dyes, are known.

These pigments and dyes, however, do not show a satisfactorily consistent safety, extent of acceptable use, or color value (black value) required as a black coloring material.

Carbon black includes Furnace Black prepared by a continuous incomplete combustion of natural gas, or a petroleum- or coal-derived heavy hydrocarbon oil, in a reaction furnace, and Channel Black prepared by burning natural gas or a hydrocarbon gas with a low flame, bringing the flame into contact with the bottom of a channel steel, resulting in a continuous flame degradation thereof that forms carbon, and recovering the carbon. Furnace Black, however, has been reported to contain benzpyrene, which is a oncogenic substance, and therefore, only Channel Black is used in the cosmetic field in Japan, and both the Channel Black and Furnace Black are prohibited to be used in the United States of America, because they are not safe black coloring materials.

Black iron oxide ($FeO \cdot Fe_2O_3$)—also called iron black—does not provide a satisfactory black value when used as a black coloring material.

Organic pigments such as aniline black are not allowed to be used in pharmaceuticals and cosmetics, from the point of view of safety.

Tar dyestuff is considered to be harmful to the human body, and therefore, the extent of the use thereof is severely limited. For example, a tar dyestuff, Black 401 prepared by lake of Naphthol Blue Black with aluminum sulfate cannot be used as a formulation to be coated on the mucous membrane, and thus the use thereof is severely limited. Moreover, Black 401 has other drawbacks in that it has a deficiency in fastness and is slightly water soluble under a neutral condition in comparison with inorganic black coloring materials such as black iron oxide.

DISCLOSURE OF THE INVENTION

The objects of the present invention are to overcome the above-mentioned drawbacks of conventional black coloring materials, and to provide a safe black coloring material having a good fastness and a very low color value, and cosmetics comprising this black coloring material.

The present invention provides a process for the production of a black coloring material, and is characterized by treating a finely powdered sugar, protein or polyamide polymer having amino groups with a naphthoquinone derivative represented by the formula (1). The resulting coloring material is a powder or gel.

In another aspect of the present invention, there are provided cosmetics containing the thus-obtained black coloring materials.

In a further aspect of the present invention, there is provided a process for staining a fiber black, characterised by treating a fiber comprising a sugar, protein or polyamide polymer having amino groups with a naphthoquinone derivative.

BRIEF EXPLANATION OF THE DRAWINGS

In FIG. 15, 1 shows a result for a nylon 6 fiber, 2 shows a result for a black-colored wool, 3 shows a result for black iron oxide, and 4 shows a result for carbon black.

BEST MODE OF CARRYING OUT THE INVENTION

Figure 1:
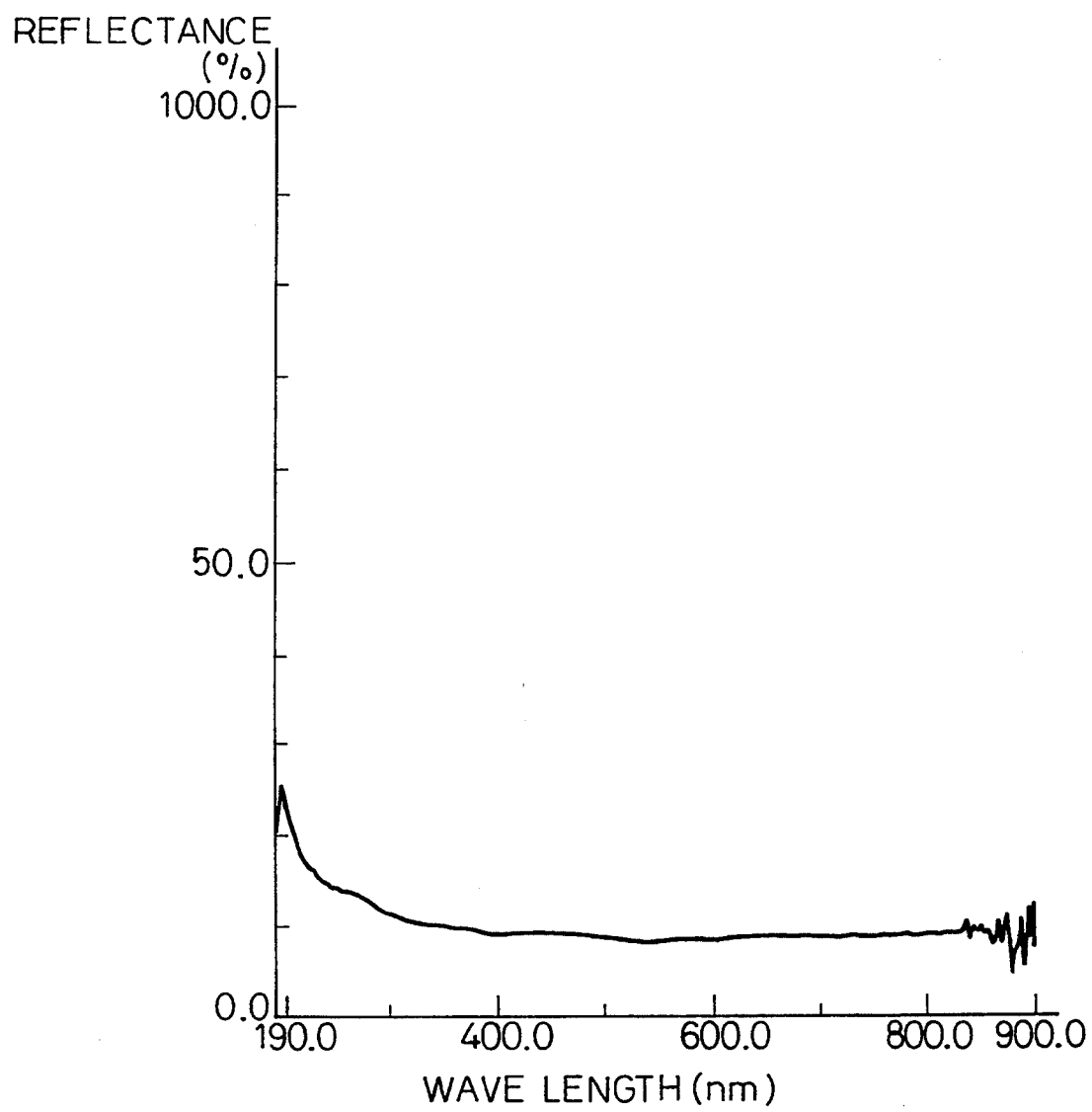
FIG. 1 represents a spectroreflectivity of the black coloring material obtained in Example 1 according to the present invention.

As finely powdered sugars having amino groups and used in the present invention, finely powdered monosaccharides such as glucosamine, galactosamine and the like, as well as polysaccharides such as finely powdered chitosan, polygalactosamine and the like are included, and among them, the chitosan is a chitosan represented by the general formula (3), wherein the acetoamide moieties bonded to the position 2 of the chitin represented by the formula (2) have been deacetylated. Partially deacetylated chitosan may be used wherein N-acethyl-D-glucosamine residues represented in the formula (2) randomly and partially remain in that molecule.

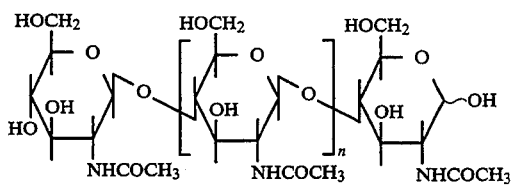 (2)

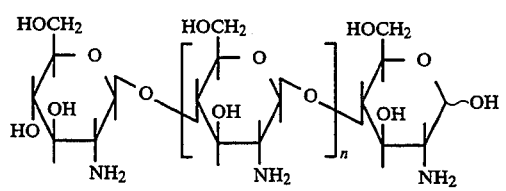 (3)

As finely powdered proteins, any polymers comprising α-amino acids linked through amide bonds (peptide bond) may be used; for example, finely powdered fur such as wool, hide such as cowhide, silk powder (silk protein, i.e., fibrin) having a size of several microns to several tens of microns, powdery casein, gelatin, soybean protein, milk protein, egg protein, and the like are included. Where gelatin dissolved in water is used according to the present invention, a gelled black coloring material is obtained, and this material can be spray-dried to obtain a powder.

Moreover, as the finely powdered polyamide polymers, nylon 6 powder and nylon 12 powder, and the like, are included.

Moreover, the fibrous sugars, protein and polyamide polymer having amino groups include artificial fibers comprising a chitosan-cellulose composite; natural fibers such as silk and wool; and artificial fibers, such as nylon 6, nylon 66, nylon 612, nylon 11, nylon 12, nylon 46, and the like. The fiber may be in the form of a staple fiber, a string, a filament, or a woven, knitted or unwoven cloth.

Naphthoquinone derivatives represented by the general formula (1):

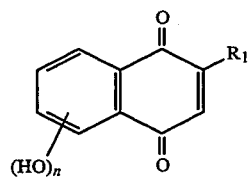 (1)

wherein $R_1$ represents a hydrogen atom, a hydroxyl group, a halogen atom, or a group represented by the following formula:

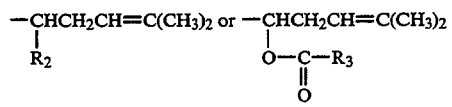

wherein $R_2$ represents a hydrogen atom or a hydroxyl group, $R_3$ represents an alkyl group, an alkenyl group or a hydroxyalkyl group, and n represents 1 or 2, and wherein the number of carbon atoms in $R_3$ is preferably up to 6, include the following compounds:

5-Hydroxy-1,4-naphthoquinone

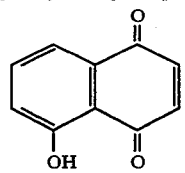

5,8-Dihydroxy-1,4-naphthoquinone

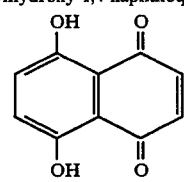

5,7-Dihydroxy-1,4-naphthoquinone

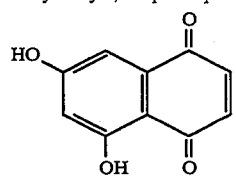

2,5,8-Trihydroxy-1,4-naphthoquine

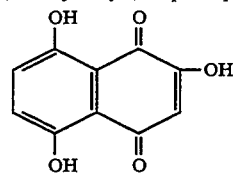

2-Chloro-5,8-dihydroxy-1,4-naphthoquinone

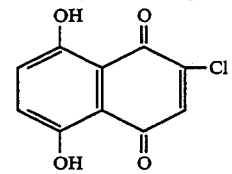

2-Bromo-5,8-dihydroxy-1,4-naphthoquinone

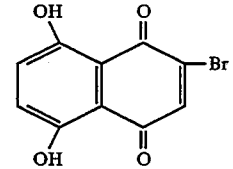

Deoxyshikonin

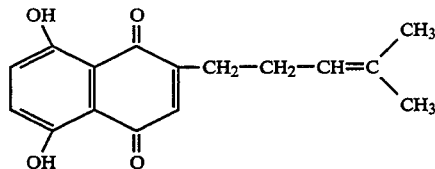

Shikonin

-continued

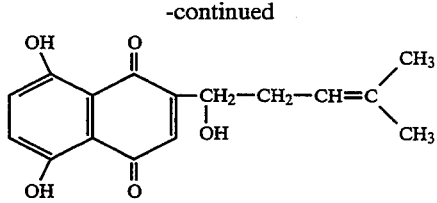

Acethylshikonin

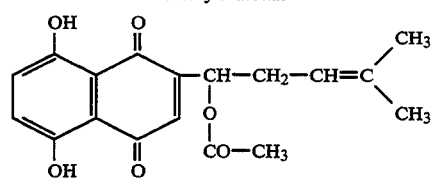

β,β-Dimethylacrylshikonin

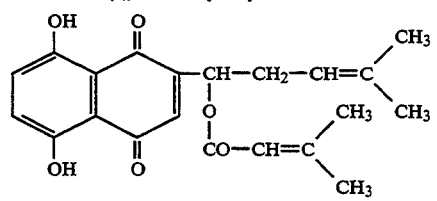

Isobutylshikonin

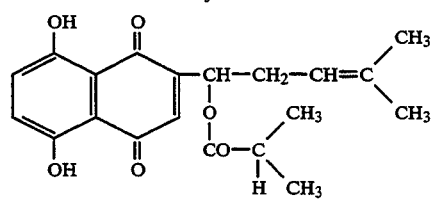

Isovalerylshikonin

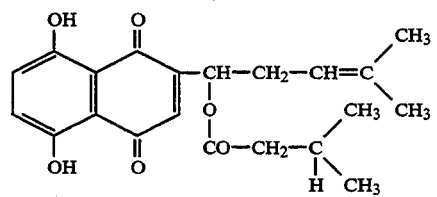

α-Methyl-n-butylshikonin

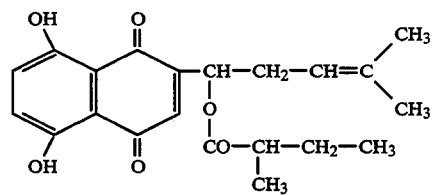

β-Hydroxyisovalerylshikonin

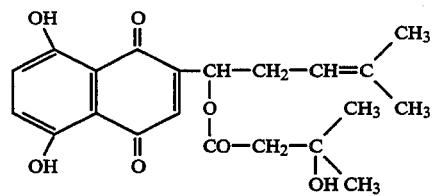

Teracrylshikonin

-continued

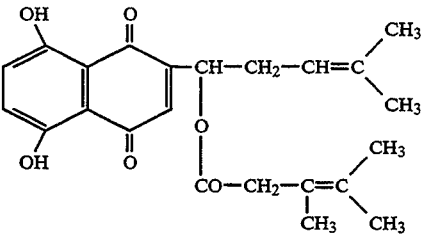

and a mixture of the above-listed shikonin, isobutylshikonin, β,β-dimethylacrylshikonin, acethylshikonin, teracrylshikonin, β-hydroxyisovalerylshikonin, and the like, prepared by extracting the root of Lithospermum with an organic solvent.

For the treatment of a finely powdered amino-containing sugar, protein or polyamide polymer with a naphthoquinone derivative represented by the general formula (1), to obtain a black coloring material, usually the finely powdered material is dispersed with stirring in a heated staining bath containing a mixture of water and an organic solvent dissolving a naphthoquinone derivative represented by the general formula (1).

Similarly, a process for obtaining black-stained fibers comprising a sugar, protein or polyamide polymer having amino groups, by treating the fiber with a naphthoquinone derivative represented by the general formula (1), is carried out by impregnating the fiber in a heated staining bath with a mixture of water and an organic solvent dissolving the naphthoquinone derivative represented by the general formula (1).

When the above treatment is carried out at a predetermined temperature for a predetermined time, the finely powdered sugar, protein or polyamide, or fiber comprising such a material is stained black.

The staining bath prepared as described above contains a mixed solvent of water and an organic solvent used to dissolve a naphthoquinone derivative represented by the above-mentioned formula (1). In this case, the ratio of water to the organic solvent is not critical, but a volume/weight ratio of the mixed solvent to a material to be stained is preferably 5 to 30.

The amount of naphthoquinone derivative used is at least 1% by weight, preferably at least 5% by weight, relative to the material to be stained, but an amount of less than 1% by weight can be used by repeating the staining process to obtain a black coloring material having a low color value, or a fiber stained to a low color value.

A staining temperature may be a room temperature, but in this case a long time is necessary for a material to be stained becoming black. Therefore, a staining temperature is maintained at 60° to 90° C. for 30 minutes to 2 hours.

It is assumed from "Dyes and Pigments", Vol. 5, pp 241–251 (1984) that the black coloring material obtained by treating a sugar, protein or polyamid polymer having amino groups with a naphthoquinone derivative represented by the above-mentioned general formula (I) is that formed by binding the sugar, protein or polyamide polymer having amino groups to the position 2 of the naphthoquinon skeleton, as shown below:

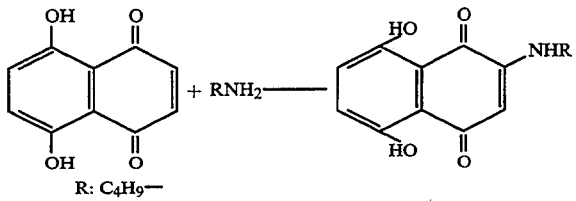

R: C₄H₉—

Another object of the present invention is to provide cosmetics containing the above-mentioned black coloring material. As the cosmetics, for example, a black soap, black pack, mascara, eyeliner, eye-shadow and the like are included. The present black coloring material also may be used as a black pigment for color-toning a cosmetic. The process for the production of cosmetics and composition of the cosmetics are conventional, except that a black coloring material produced by the present process is used.

EXAMPLES

Next, the present invention is described in detail by Examples.

Note, the diffuse reflectance spectrum of a sample obtained in each Example was measured by a visible light-ultraviolet spectrophotometer using an integrating sphere (Nippon Bunko Kogyo; spectrophotometer Ubest 50).

Among compounds used as naphthoquinone derivatives represented by the formula (I), a mixture of shikonin, isobutylshikonin, β,β-dimethylacrylshikonin, acetylshikonin, teracrylshikonin, β-hydroxyisovalerylshikonine and the like was prepared by extracting "Shikon" (the root of Lithospermum; the place of production: China; the type: fresh) in the Japanese Pharmacopoeia with an organic solvent according to the following Example for Preparing a Naphthoquinone Derivative, purified, developed by a thin layer chromatography using chloroform as a developer, and identified on the basis of an Rf value according to the Natural Dyestuff Handbook, published by Korin, pp 396–397.

Example for Preparing Mixture of Naphthoquinone Derivatives

First, 1 kg of dried "Shikon" (the root of Lithospermum; the place of production: China; the type: fresh) was sliced into small pieces and put into a 20 liter cylindrical container made of stainless steel with a cover, and then 5 l of ethanol (purify 99.5%) as an extraction solvent was added thereto. The mixture was allowed to stand for 3 days at a room temperature without sealing, and then filtered to obtain 4,410 ml of an ethanol extract having a deep reddish-violet color.

Next, 300 ml of the extract was evaporated and concentrated under a reduced pressure, to remove ethanol, and 3.29 of a syrup-like pigment extract (concentrate) having a deep reddish-violet color was obtained.

An amount of pigment extracted from Shikon contained in the alcohol extract solution was 1.07% (W/V %), and an extraction ratio was 4.70% (W/W %) on the basis of the dried Shikon (the root of Lithospermum) used. Then, 20 g of the syrup-like deep-reddish violet pigment extract (concentrate) of Shikon obtained as above was applied to a 45 mmφ×750 mm glass chromatographic column filled with 200 g of silica gel (Merck Kieselgel 60, 70–230 mesh) and eluted with chloroform. Fractions of the elute having a red color were combined and concentrated under a reduced pressure, to obtain 7.2 g of an dark-red syrup.

The dark-red syrup thus obtained was developed on a thin layer chromatography plate (Merck, silicagel G) using chloroform as a developing solvent, according to a method described in Natural Coloring Material Handbook, ed. Tanimura, published on Jun. 25, 1979, pp 396–397.

This thin layer chromatography provided 6 spots corresponding to the approximate Rf values of 0.85, 0.78, 0.52, 0.36, 0.18 and 0.05, which conformed to the Rf values of isobutylshikonin, β,β-dimethylacrylshikonin, acetylshikonin, teracrylshikonin, shikonin and β-hydroxyisovalerylshikonin disclosed respectively in the above-cited Handbook.

EXAMPLE 1

(1) 100 ml of methanol was put into a 200 ml conical flask, to which was added 6 g of D-glucosamine hydrochloride and 5 g of sodium metoxide, the mixture was stirred at a room temperature for one hour, and the resulting insoluble matter (sodium chloride) was filtered off to obtain a solution of free D-glucosamine.

(2) 50 ml of water was put into a 200 ml 3-necked round-bottomed flask equipped with a condenser, a thermometer and a stirrer, to which was added 1 g of shikonin obtained from Lithospermum by cell culture method (Mitsui Petrochemical) previously dissolved in 100 ml of ethanol to form a staining bath. Next, to the staining bath was added all of the D-glucosamine solution obtained in (I), and the mixture was refluxed at 85° C. to 90° C. for one hour, with stirring.

After the refluxing with heating, the whole solution in the staining bath was concentrated to obtain a solid, which was then ground with a mortar to obtain a finely powdered black coloring material.

A spectroreflectivity of the obtained black coloring material is shown in FIG. 1, and this confirmed that the material absorbs at least 90% of the light over the entire visible light range (380 to 780 nm).

EXAMPLE 2

First, 50 ml of water was added to a 200 ml 3-necked round-bottomed flask equipped with a condenser, a thermometer and a stirrer, to which was added 0.5 g of 5-hydroxy-1,4-naphthoquinone dissolved in 50 ml of ethanol to form a staining bath. At this time, the pH value of the mixture in the staining bath was 4.9.

Next, 5 g of white powder of chitosan (Chitosan PSL: extent of deacethylation 78.1%; Yaizu Suisan Kagaku) was put into the staining bath, and the mixture was refluxed with heating at a temperature of 85° C. to 90° C. for one hour, while stirring. The pH value of the mixture in the staining bath was 7.2.

After the refluxing with heating, a black-colored chitosan was separated and dried at 50° C. to 55° C., to obtain a residue, which was then ground with a mortar to obtain a finely powdered black color material.

Figure 2:
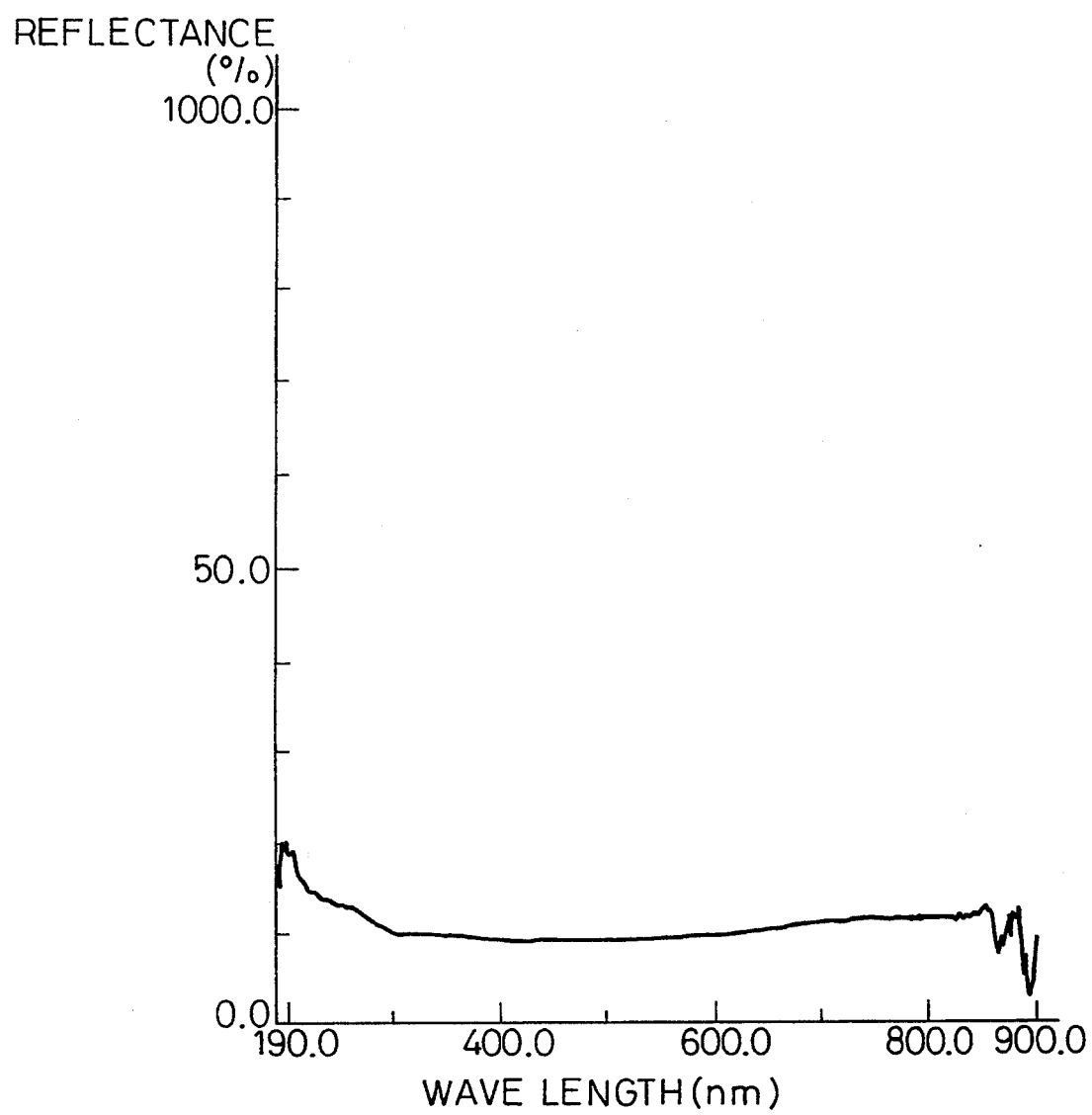
FIG. 2 represents a spectroreflectivity of the black coloring material obtained in Example 2 according to the present invention.

The spectroreflectivity of the obtained black coloring material is shown in FIG. 2, and this confirmed that the material absorbs about 90% of the light over the entire visible light range (380 nm to 780 nm).

EXAMPLES 3 TO 5

Chitosan was treated in the same manner as Example 2, under the conditions shown in Table 1. The results are shown in Table 1.

Figure 3:
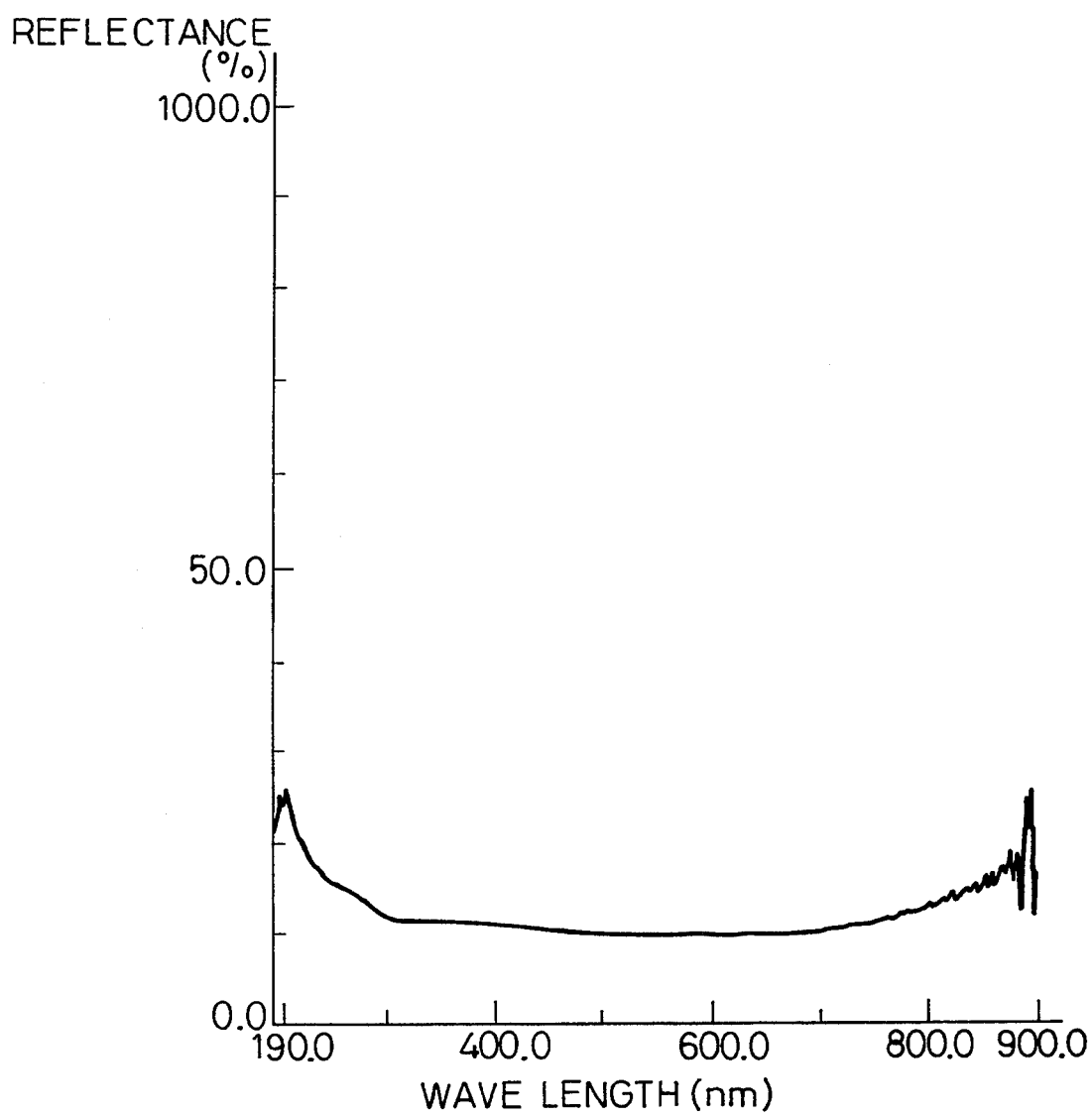
FIG. 3 represents a spectroreflectvitity of the black coloring material obtained in Example 3 according to the present invention.
Figure 4:
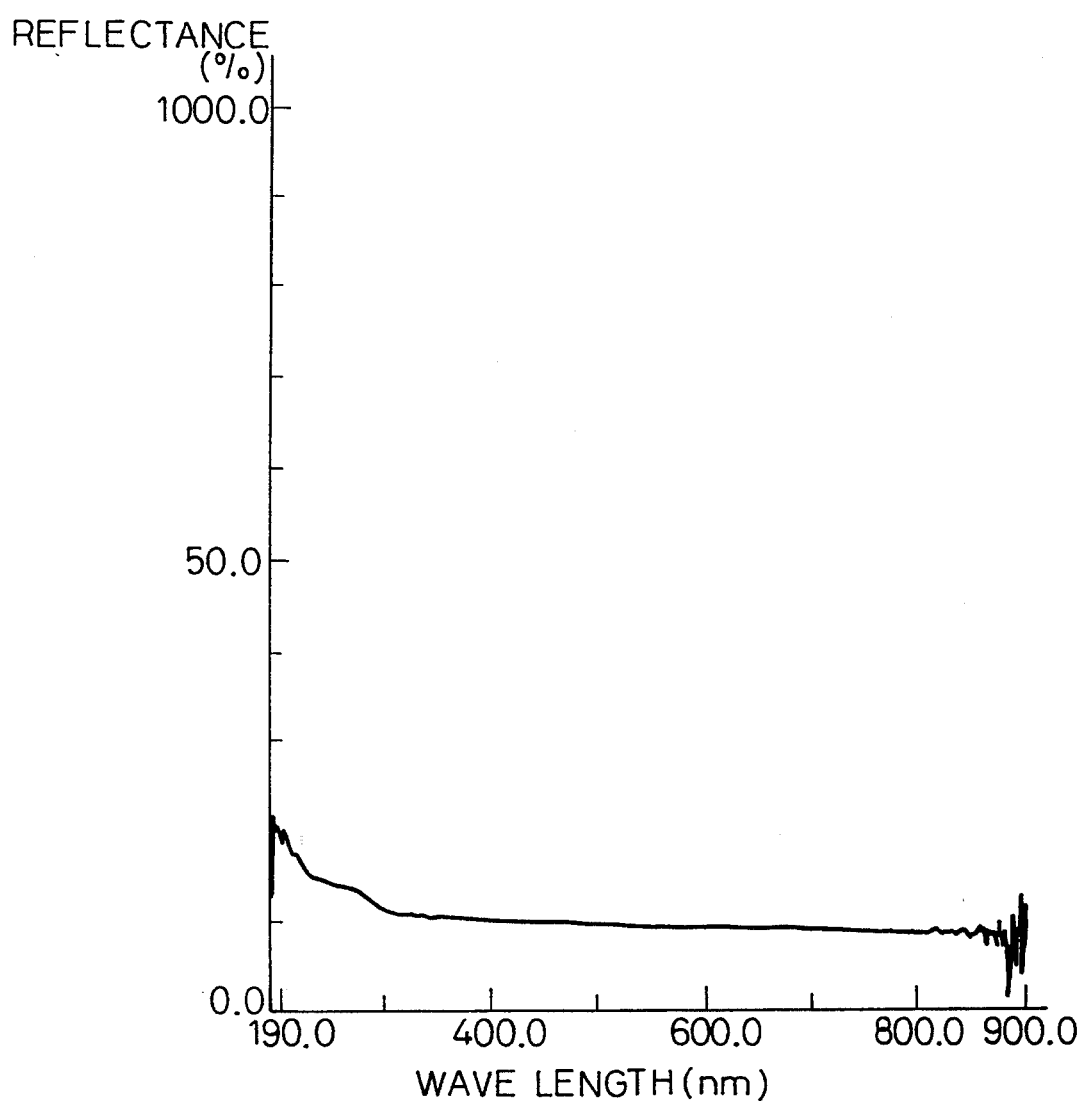
FIG. 4 represents a spectroreflectvitity of the black coloring material obtained in Example 4 according to the present invention.
Figure 5:
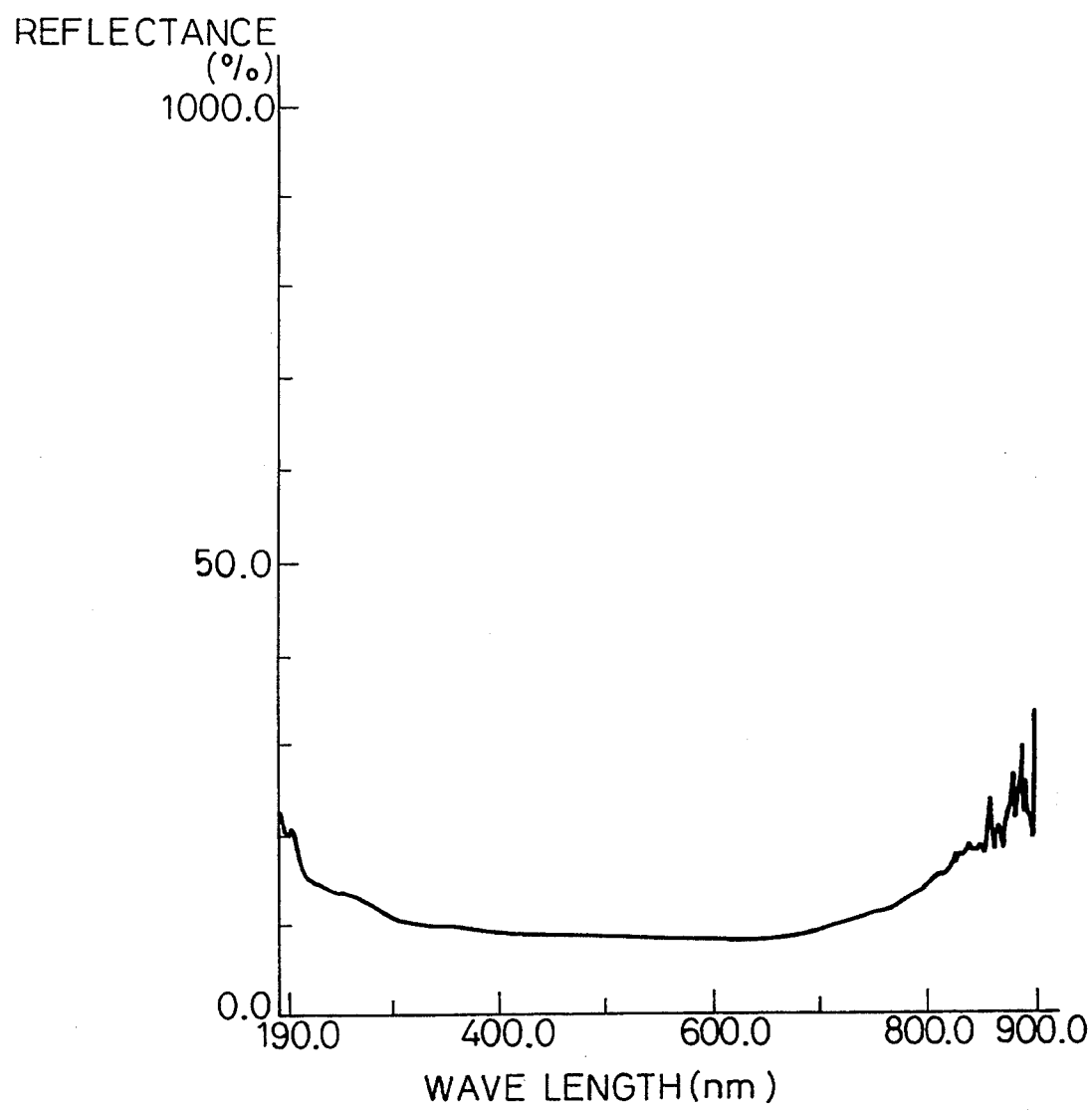
FIG. 5 represents a spectroreflectvitity of the black coloring material obtained in Example 5 according to the present invention.

The spectroreflectivity of the obtained black coloring materials are shown in FIG. 3 (Example 3), FIG. 4 (Example 4), and FIG. 5 (Example 5).

TABLE 1

| | | Example No. | | |
|---|---|---|---|---|
| | | 3 | 4 | 5 |
| Naphthoquinone derivative and amount used | | 5,8-Dihydroxy-1,4-naphthoquinone 0.5 g | 5,8-Dihydroxy-1,4-naphthoquinone 0.15 g | Shikonin 1 g |
| Amount of chitosan used | | 5 g | 1.5 g | 10 g |
| Staining bath Condition | Water | 50 ml | 15 ml | 180 ml |
| | Ethanol | 50 ml | 15 ml | 22 ml |
| | Temperature | 78–82° C. Reflux | 78–82° C. Reflux | 80–85° C. Reflux |
| | Time | 60 minutes | 60 minutes | 60 minutes |
| Appearance of colored product | | Black | Black | Black |

EXAMPLE 6

(1) 100 ml of water was put into a 200 ml beaker, in which 10 g of gelatin was dissolved, to prepare a viscose gelatin solution.

(2) The whole gelatin solution prepared in (1) was put into a 200 ml 3-necked round bottomed flask, to which was added 1 g of the naphthoquinone mixture prepared according to the above-described "Example for Preparing Mixture of Naphthoquinone Derivatives" and dissolved in 20 ml of ethanol, and the resulting mixture was refluxed with heating at 85° C. to 90° C. for 2 hours, while stirring. The gelatin in the staining bath was stained black, and after cooling, a gelled black coloring material was obtained.

Figure 6:
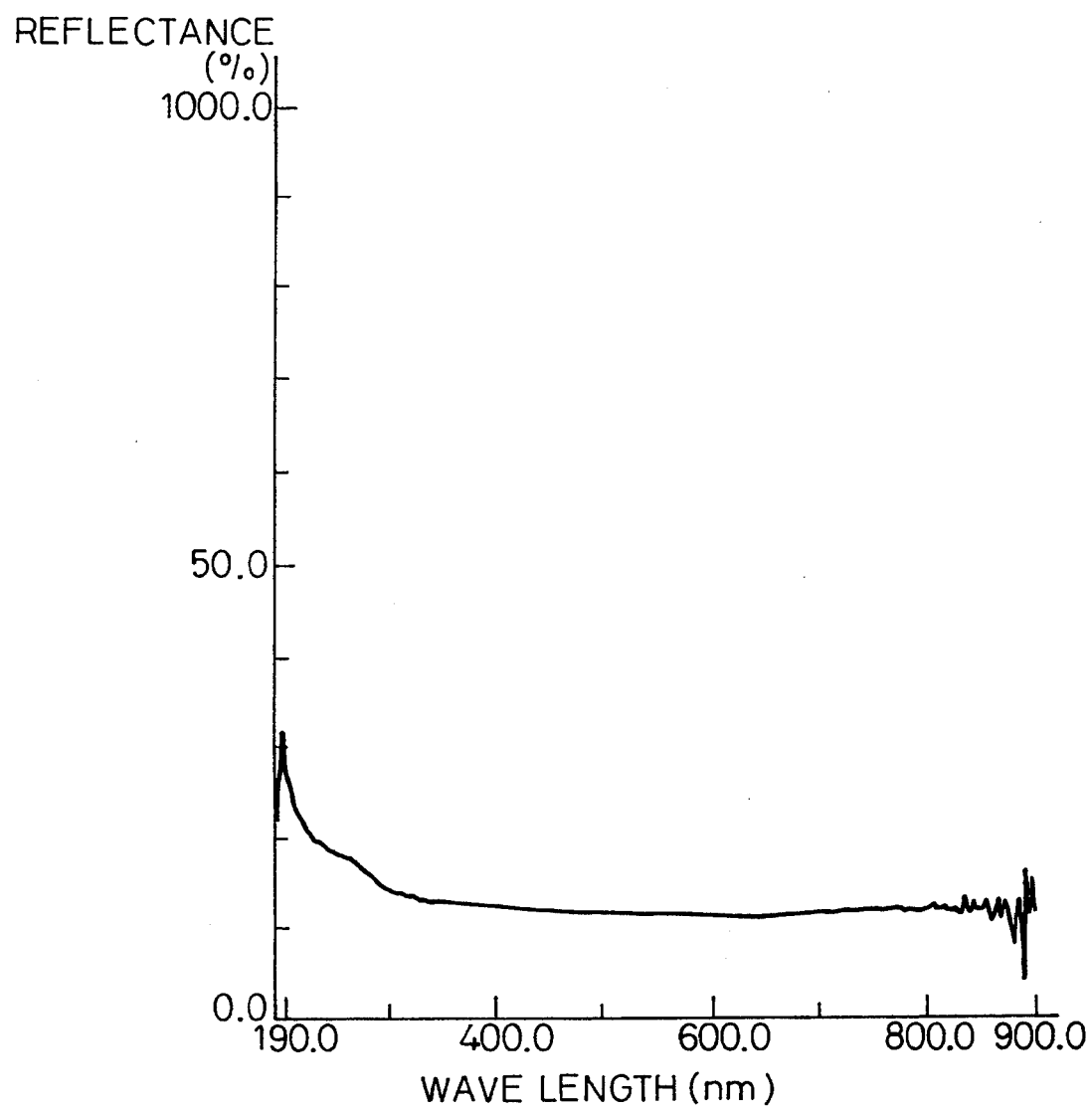
FIG. 6 represents a spectroreflectivity of the black coloring material obtained in Example 6 according to the present invention.

The spectroreflectivity of the obtained black coloring material is shown in FIG. 6, and it was confirmed that the product absorbs about 90% of the light over an entire visible light range (380 nm to 780 nm).

EXAMPLE 7

Water in an amount of 200 ml was put into a 500 ml 3-necked round-bottomed flask, to which was added 2 g of the naphthoquinone derivative mixture obtained according to the above-described "Example for Preparing Mixture of Naphthoquinone Derivatives" and dissolved in 200 ml of ethanol, to prepare a staining bath. Next, 20 g of white powder of casein was put into the flask, and the mixture was refluxed with heating at 80° C. to 85° C. for one hour. The casein in the staining bath changed to black, and after refluxing with heating, a black-stained casein powder was separated, and dried at 50° C. to 55° C., to obtain a finely powdered black coloring material.

Figure 7:
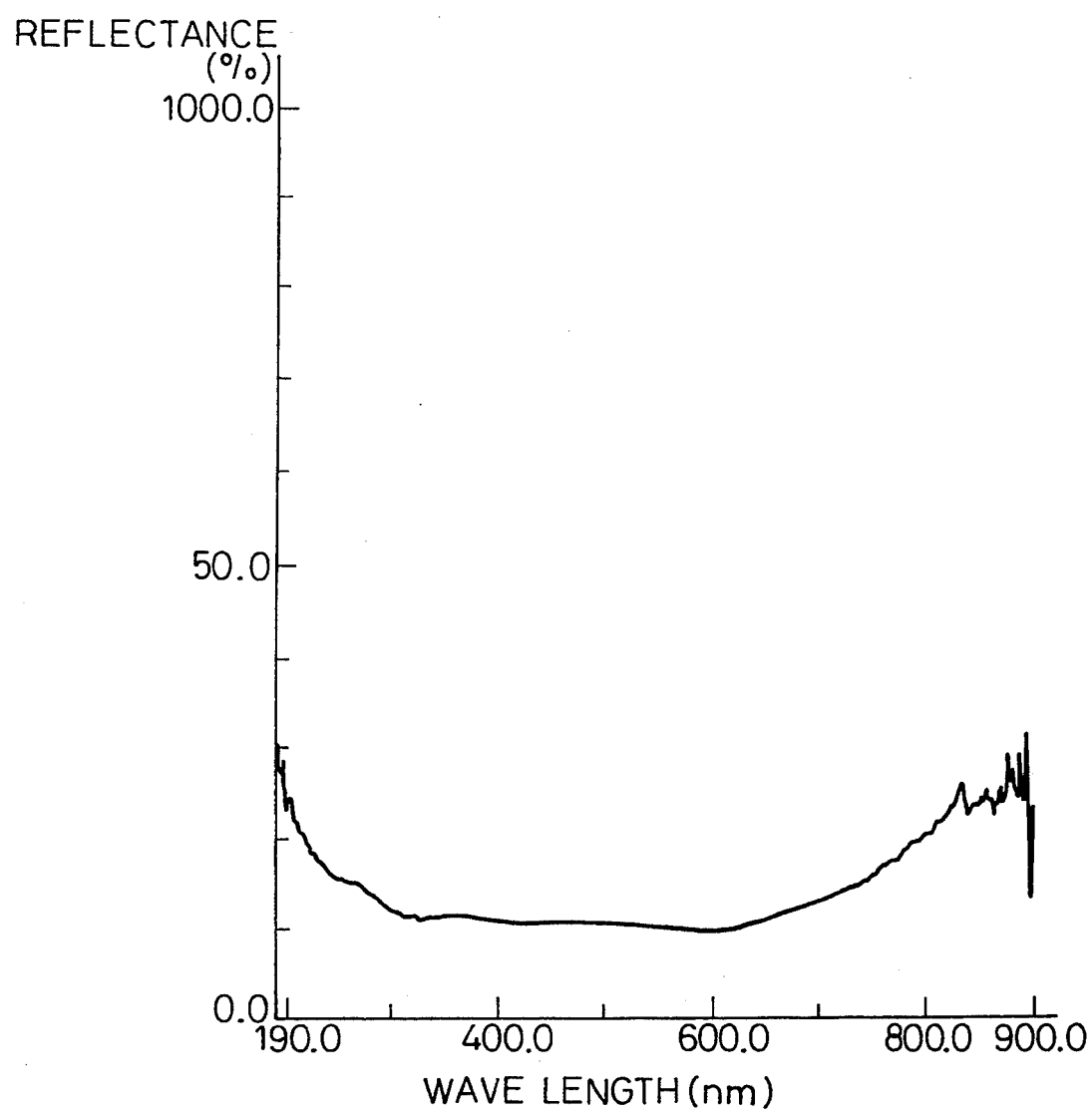
FIG. 7 represents a spectroreflectivity of the black coloring material obtained in Example 7 according to the present invention.

The spectroreflectivity of the obtained black coloring material is shown in FIG. 7.

EXAMPLE 8

The same procedure as described in Example 7 was repeated, except that silk powder (silk protein (Kanebo Kenshi Kyo-bizin K.K., KANEBO SILK POWER H, average particle size 6 to 7μ) was used in place of casein, to obtain a finely powdered black coloring material.

The obtained black coloring material was black.

Figure 8:
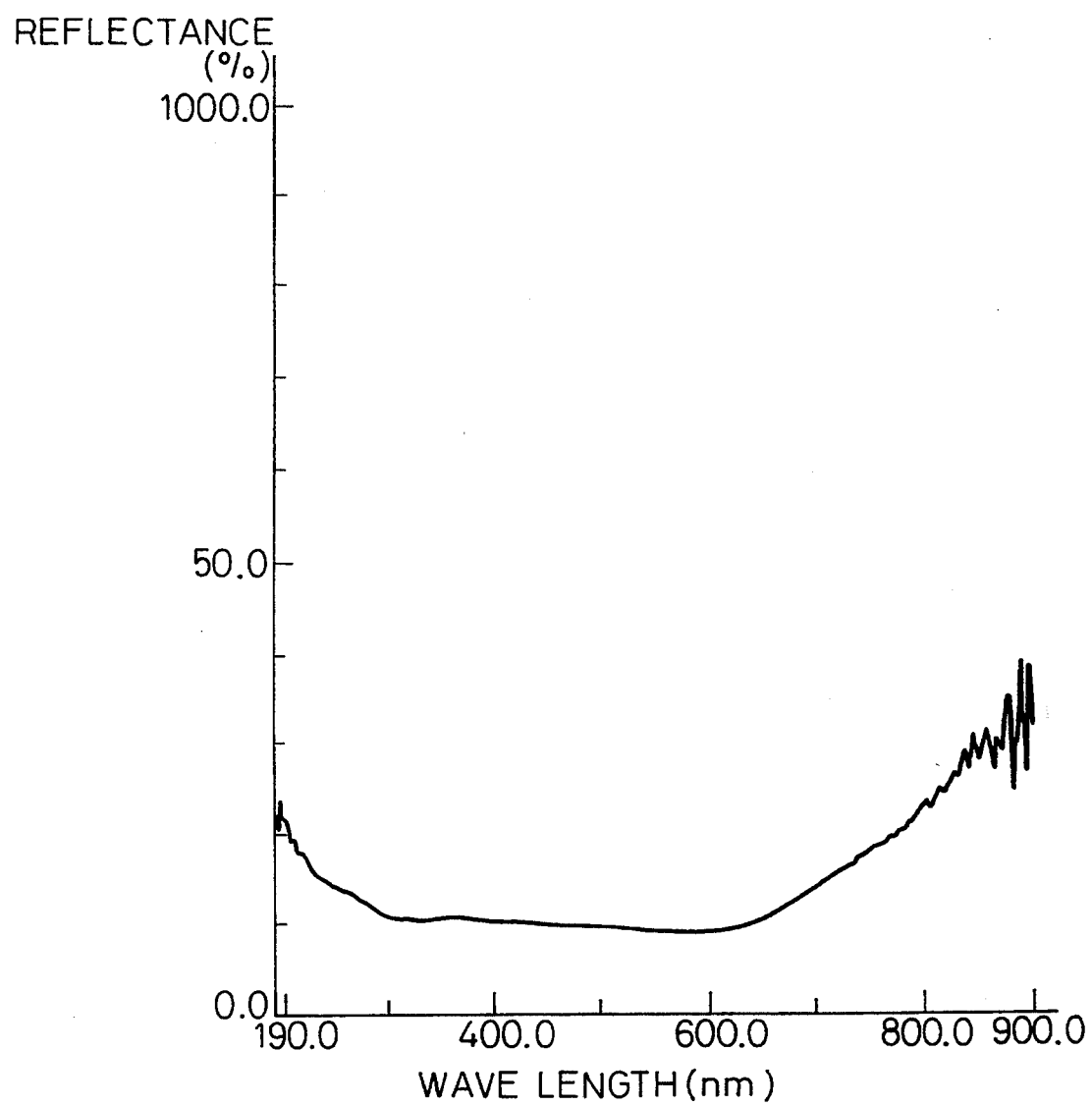
FIG. 8 represents a spectroreflectivity of the black coloring material obtained in Example 8 according to the present invention.

The spectroreflectivity of the obtained black coloring material is shown in FIG. 8.

EXAMPLE 9

The same procedure as described in Example 7 was repeated except that Nylon 12 powder was used in place of casein, to obtain a finely powdered black coloring material.

Figure 9:
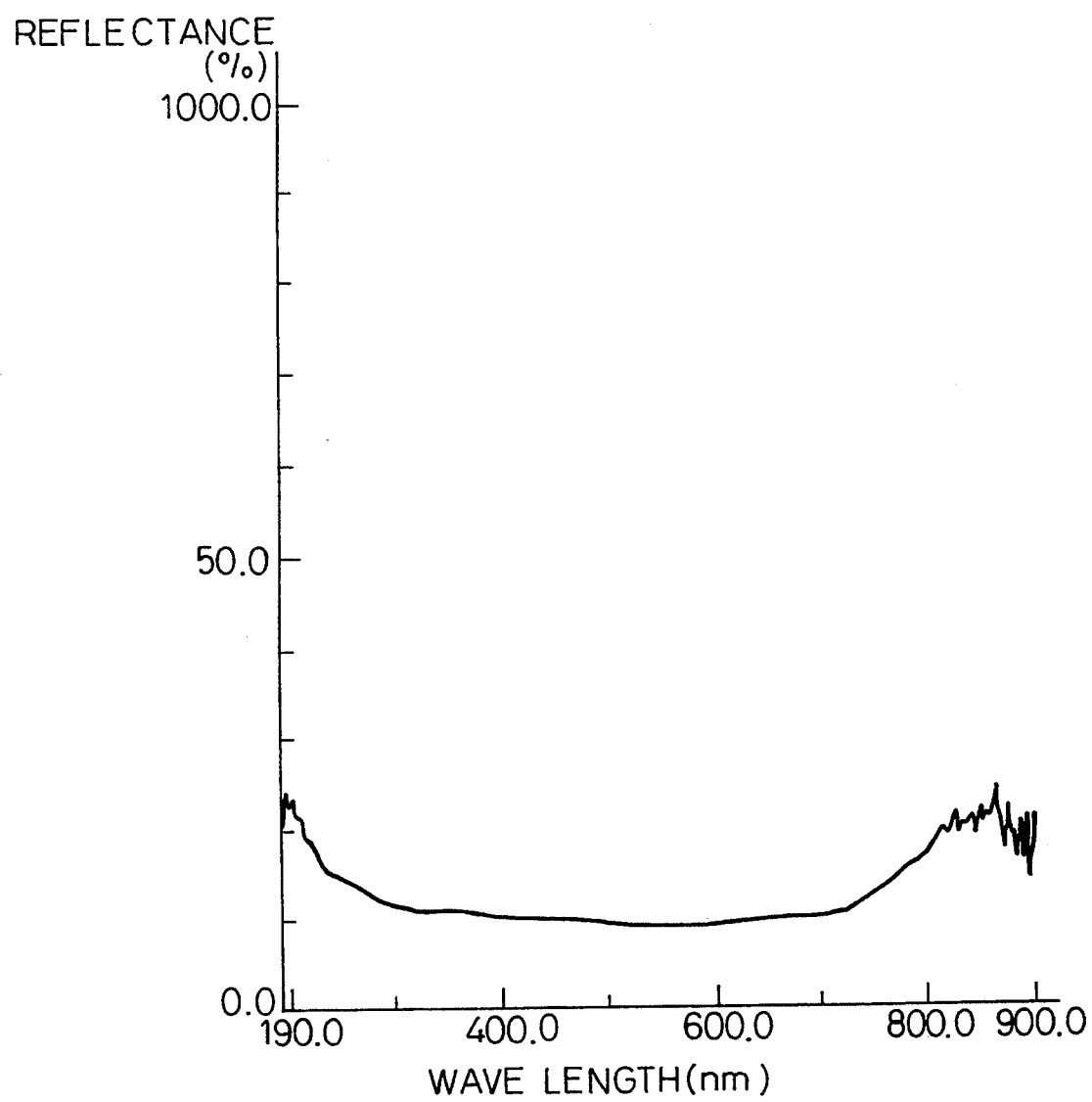
FIG. 9 represents a spectroreflectivity of the black coloring material obtained in Example 9 according to the present invention.

The spectroreflectivity of the obtained black coloring material is shown in FIG. 9.

EXAMPLE 10

The same procedure as described in Example 7 was repeated except that Nylon 6 powder was used in place of casein, to obtain a finely powdered black coloring material.

Figure 10:
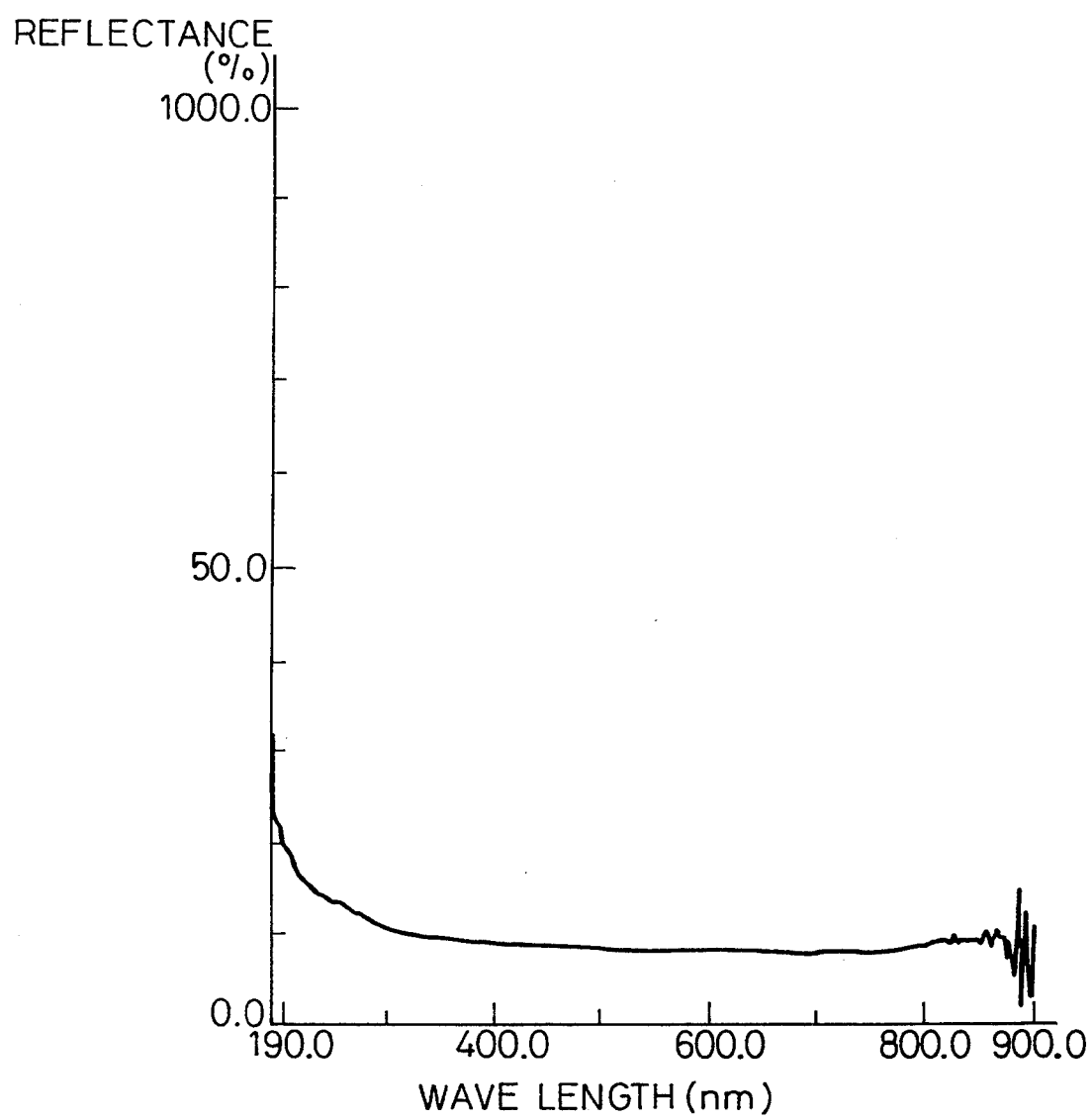
FIG. 10 represents a spectroreflectivity of the black coloring material obtained in Example 10 according to the present invention.

The spectroreflectivity of the obtained black coloring material is shown in FIG. 10.

EXAMPLE 11

The same procedure as described in Example 7 was repeated except that Nylon 6 powder was used in place of casein, and shikionin (Mitsui Petrochemical) obtained by a cell culture of Lithospermum was used in place of the naphthoquinone derivative mixture, to obtain a finely powdered black coloring material.

Figure 11:
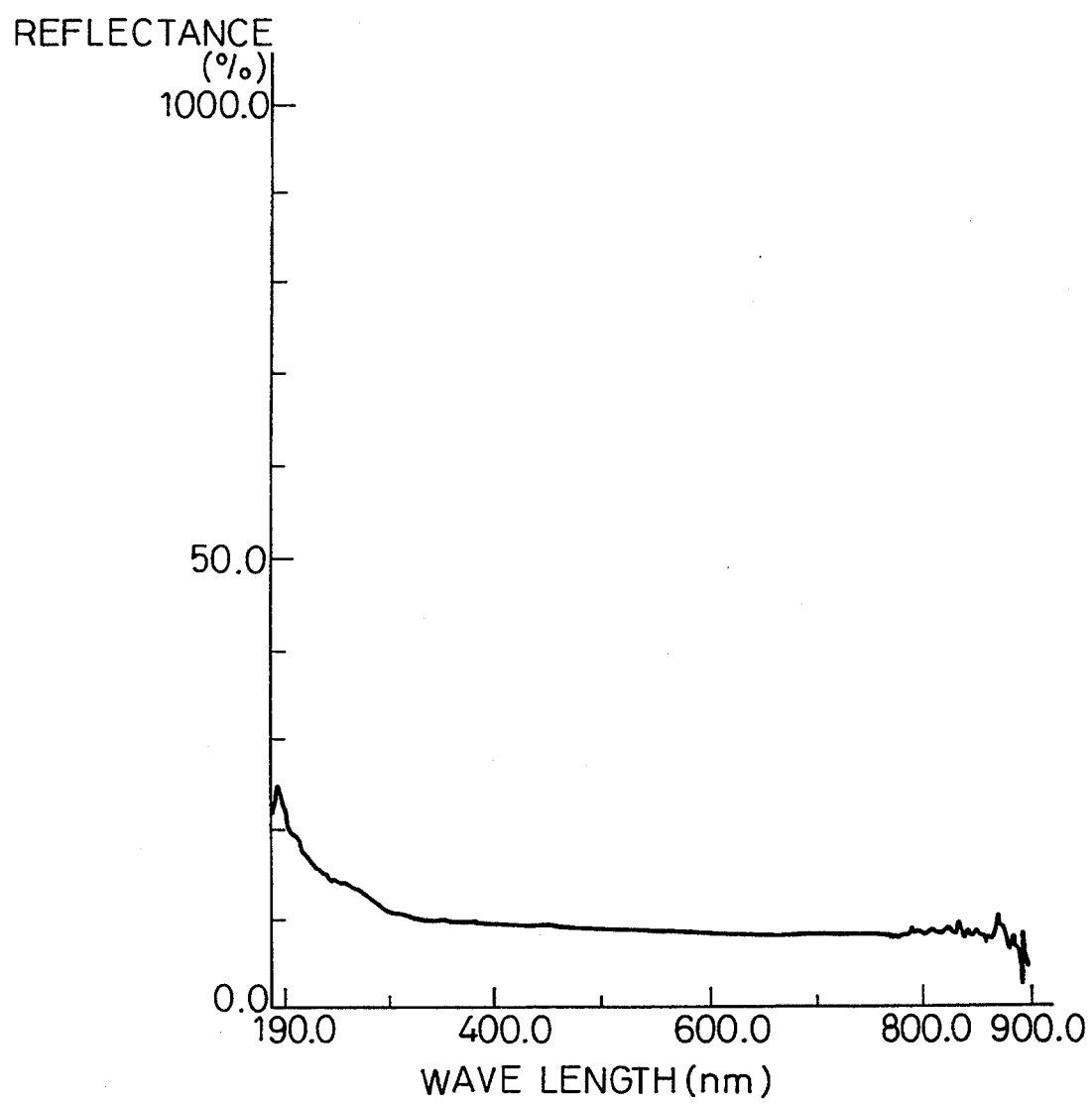
FIG. 11 represents a spectroreflectivity of the black coloring material obtained in Example 11 according to the present invention.

The spectroreflectivity of the obtained black coloring material is shown in FIG. 11.

EXAMPLE 12

The same procedure as described in Example 7 was repeated except that Nylon 6 powder was used in place of casein, and 5,8-dihydroxy-1,4-naphthoquinone was used in place of the naphthoquinone derivative mixture, to obtain a finely powdered black coloring material.

Figure 12:
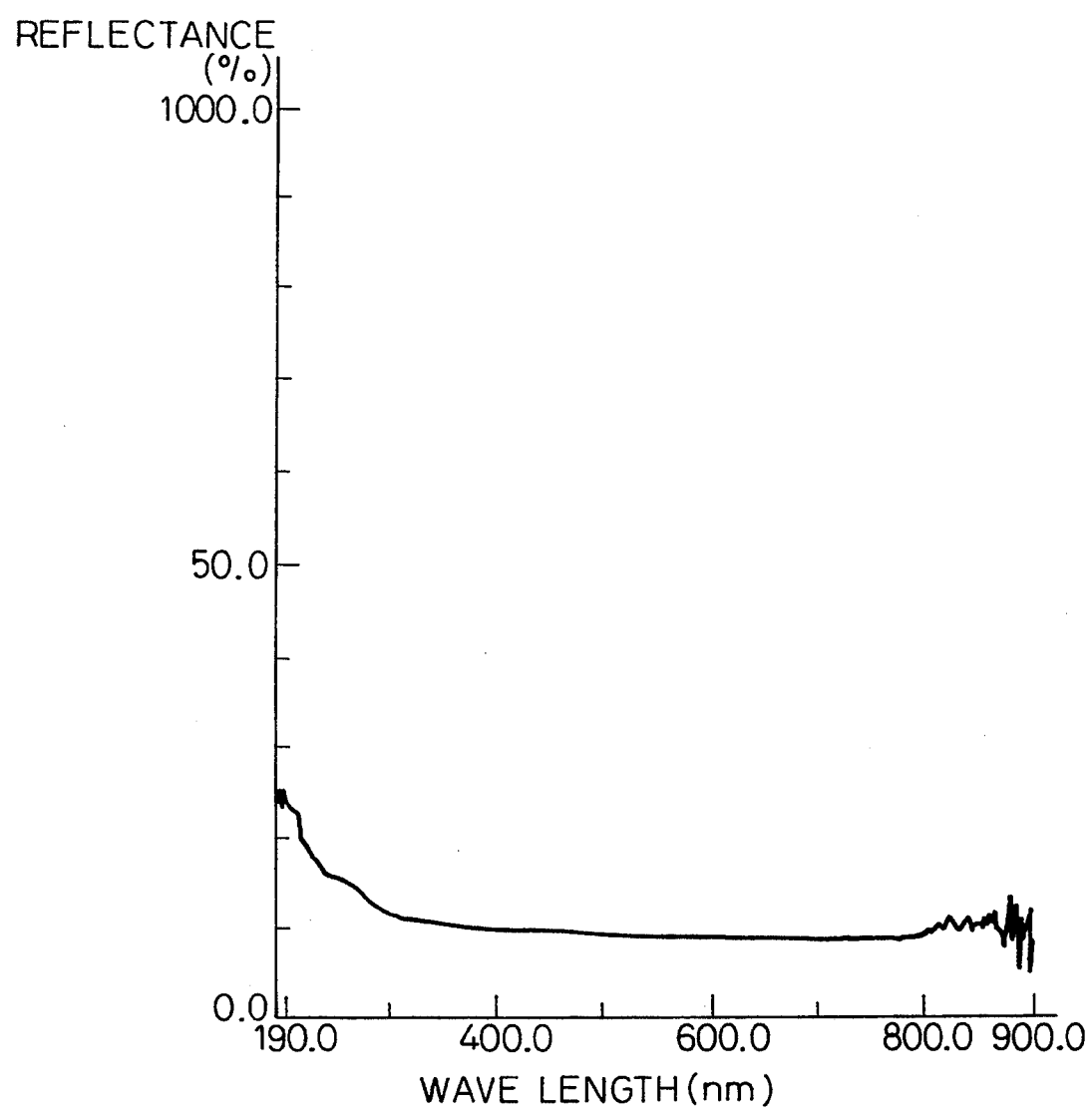
FIG. 12 represents a spectroreflectivity of the black coloring material obtained in Example 12 according to the present invention.

The spectroreflectance of the obtained black coloring material is shown in FIG. 12.

EXAMPLE 13

The same procedure as described in Example 7 was repeated, except that Nylon 6 powder was used in place of casein, and 2-chloro-5,8-dihydroxy-1,4-naphthoquinone was used in place of the naphthoquinone derivative mixture, to obtain a finely powdered black coloring material.

Figure 13:
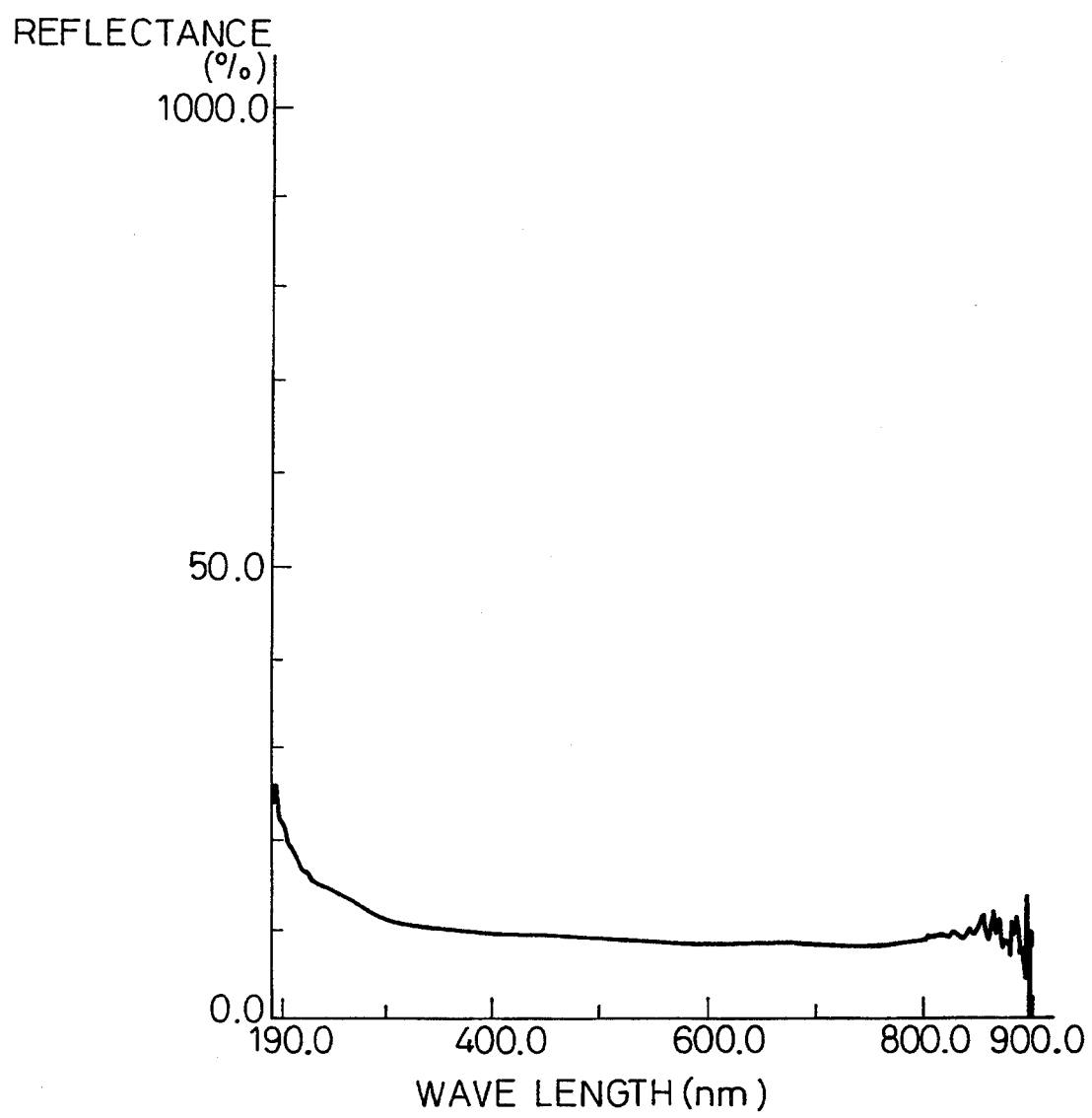
FIG. 13 represents a spectroreflectivity of the black coloring material obtained in Example 13 according to the present invention.

The spectroreflectivity of the obtained black coloring material is shown in FIG. 13.

EXAMPLE 14

Water in an amount of 200 ml was put into a 500 ml beaker, to which was added 1 g of shikonin (Mitsui Petrochemical) obtained by a cell culture of Lithospermum and dissolved in 50 ml of ethanol, to prepare a staining bath. Then 5 g of Nylon 6 fiber (string: 13 deniers) was soaked in the staining bath and heated at 85° C. to 95° C. for 30 minutes, with gentle stirring. The fiber in the staining bath was stained black. The stained fiber was then washed in hot water and dried in air, to obtain a black fiber.

The black fiber thus obtained had been homogeneously stained black, and had light fastness.

Figure 14:
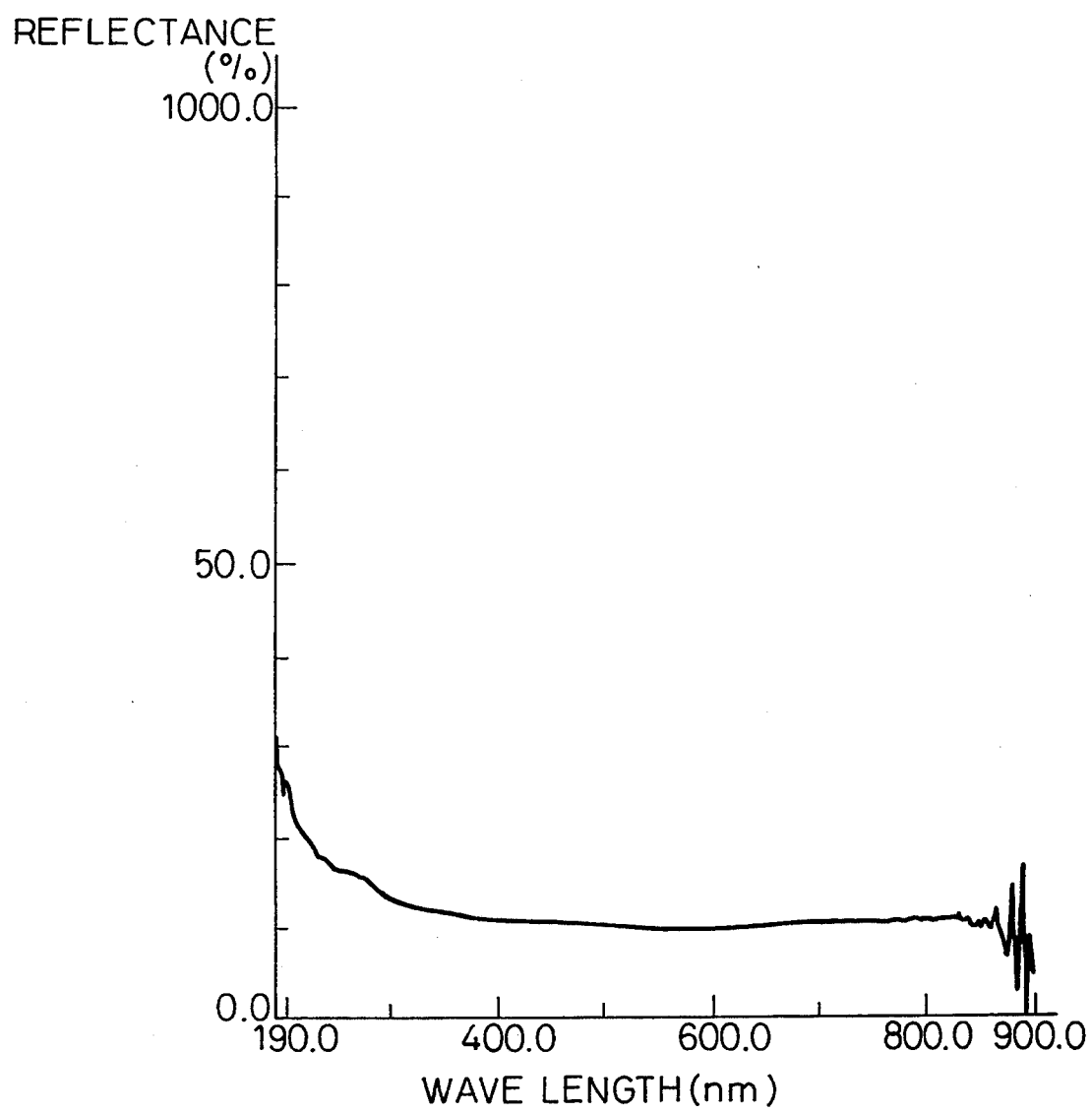
FIG. 14 represents a spectroreflectivity of the black-colored fiber obtained in Example 14 according to the present invention.

The spectroreflectivity of the obtained black fiber is shown in FIG. 14, and this confirmed that the fiber absorbs about 90% of the light over an entire visible light range (380 nm–780 nm).

EXAMPLE 15

Water in an amount of 200 ml was put into a 500 ml beaker, to which was then added 5 g of wool fiber that had been cut into 3 to 5 mm sections, and the mixture was heated at 55° C. to 60° C. for 30 minutes, with stirring.

Next, 1 g of shikonin (Mitsui Petrochemical) obtained by a cell culture of Lithoxpermum and dissolved in 50 ml ethanol was added to the beaker, which was then heated at 87° C. to 89° C. for one hour, with gentle stirring. The wool fiber in the staining bath was stained black. After the refluxing with heating, the black-stained wool was taken out, gently squeezed, and then dried, to obtain black fibers.

Figure 15:
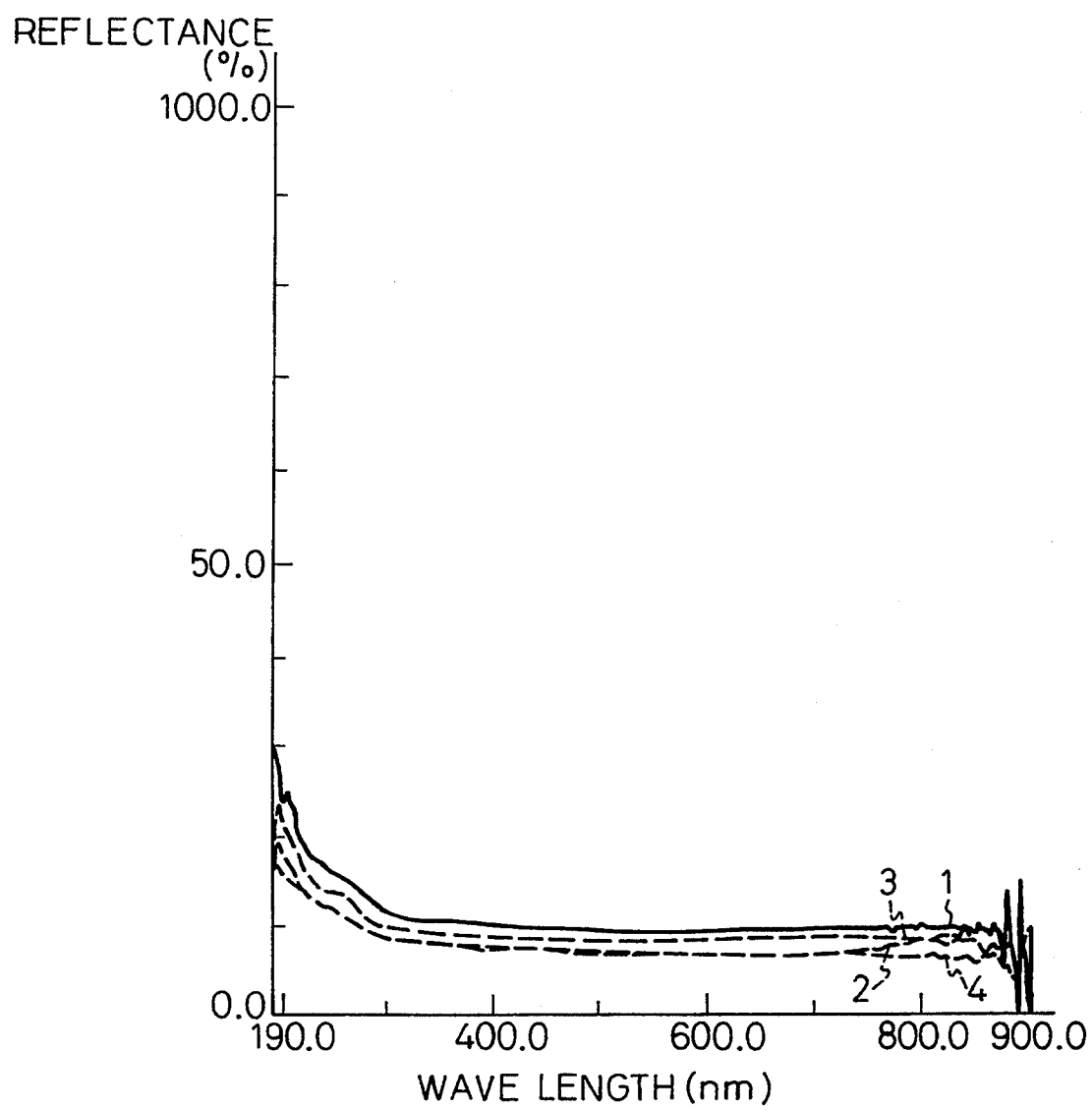
FIG. 15 represents a spectroreflectivity of the black-colored fiber and other black coloring materials obtained in Example 15 according to the present invention.

The obtained black fibers had a deep black color, and when compared with the Nylon 6 black fiber obtained in Example 14, and conventional black coloring materials, i.e., finely powdered black iron oxide (MAPICO Black BL-100; Titan Kogyo) and carbon black (Carbon Black Special - 6; Degussa) with respect to the spectroreflectivity thereof, as shown in FIG. 15, the black fiber (No. 2) of this Example absorbed more light than the Nylon 6 black fiber (No. 1) and the conventional black coloring materials, i.e., finely powdered black iron oxide (No. 3), and had a black color more than the same as that of the carbon black (No. 4).

Example for Preparation of Cosmetics 1. (Production of Mascara)

A mascara was produced according to the following recipe.
(1) Propylene glycol: 3 part by weight
(2) Polyvinyl alcohol: 2 part by weight
(3) Colloidal water-containing magnesium aluminum silicate: 1 part by weight
(4) Black coloring material of the present invention obtained in Example 1: 15 part by weight
(5) Titanum oxide: 2 part by weight
(6) Triethanol amine: 2 part by weight
(7) Stearic acid: 3 part by weight
Breached beewax: 7 part by weight
(9) Cetyl alcohol: 3 part by weight
(10) Carnaba wax: 2 part by weight According to the above-mentioned recipe, first (1) to (3) were added to 60 parts by weight of purified water and dissolved therein by heating to 80° C. Then (4) to (6) were homogeneously dispersed in the solution, and further, (7) to (10) were added and emulsified therein. The resulting mixture was homogeneously mixed, cooled to a room temperature, and filled in a container to thus produced a mascara article.

If necessary, an appropriate amount of a preservative such as butyl paraoxybenzoate or methyl paraoxybenzoate may be added to the mascara.

Example for Preparation of Cosmetics 2. (Production of Black Pack)

A black pack was produced according to the following recipe.
(1) Vinylacetate resin emulsion: 15 part by weight
(2) Polyvinyl alcohol: 10 part by weight
(3) Olive oil: 3 part by weight
(4) Glycerin: 5 part by weight
(5) Kaolin: 10 part by weight
(6) Black coloring material of the present invention obtained in Example 11: 15 part by weight
(7) Ethanol: 5 part by weight
(8) Purified water: 37 part by weight According to the above-mentioned recipe, first, polyvinyl alcohol was wetted with a part of the ethanol, and the wetted polyvinyl alcohol then added to purified water in which kaolin and the present black coloring material obtained in Example 11 had been dispersed. The mixture was heated to 70° C., and allowed to stand overnight while sometimes stirring. On the next day, glycerin, vinyl acetate emulsion and olive oil dissolved in the remaining part of ethanol were added thereto and the whole was mixed to form homogenous paste, which was then filled to containers to produce black pack articles.

If necessary, an appropriate amount of a preservative and a perfume may be added at the same time as the olive oil is added.

Example for Preparation of Cosmetics 3. (Production of Black Soap)

A black transparent soap was produced according to the following recipe.
(1) Tallow: 22 parts by weight
(2) Coconut oil: 10 parts by weight
(3) Castor oil: 4 parts by weight
(4) Olive oil: 4 parts by weight
(5) Sodium hydroxide: 6 parts by weight (saponification equivalent)
(6) Ethanol: 20 parts by weight
(7) Purified water: 15 parts by weight
(8) Sugar: 9 parts by weight
(9) Glycerine: 4 parts by weight
(10) Present black coloring material obtained in Example 6: 6 parts by weight According to the above-mentioned recipe, first, tallow, coconut oil, castor oil and olive oil were mixed, and to the mixture were added ethanol and purified water. The resulting mixture was then stirred to carry out a saponification reaction, and thereafter, sugar and glycerin were added thereto and dissolved with stirring. Next, the present black coloring material produced in Example 6 was added thereto and the whole was well kneaded, cooled, dried in air at a room temperature for 50 days and then molded, to thus prepare a black soap.

If necessary, an appropriate amount of perfume and metal ion cheleting agent may be added to the above-mentioned black soap.

Industrial Applicability

The present black coloring materials are useful as a component of cosmetics, etc.

We claim:
1. A process for production of a black coloring material comprising
treating a finely powdered sugar having amino groups,
with a naphthoquinone derivative represented by the general formula:

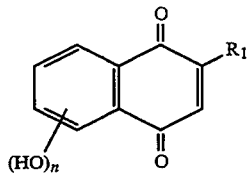

wherein $R_1$ represents a hydrogen atom, a hydroxyl group, a halogen atom, or a group represented by the following formula:

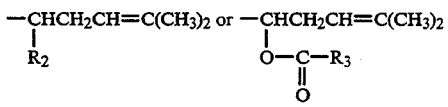

wherein R$_2$ represents a hydrogen atom or a hydroxyl group, R$_3$ represents an alkyl group, an alkenyl group or a hydroxylalkyl group, and n represents 1 or 2.

2. A cosmetic comprising a black coloring material produced by the process of claim 1.

3. A process for staining fiber to impart a black coloring comprising
   treating a fiber having amino groups,
   said fiber comprising sugar,
   with a naphthoquinone derivative represented by the general formula:

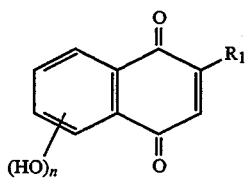

wherein R$_1$ represents a hydrogen atom, a hydroxyl group, a halogen atom, or a group represented by the following formula:

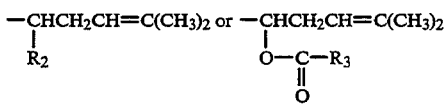

wherein R$_2$ represents a hydrogen atom or a hydroxyl group, R$_3$ represents an alkyl group, an alkenyl group or a hydroxylalkyl group, and n represents 1 or 2.

4. The process of claim 1 wherein the finely powdered sugar comprises glucosamine, galactosamine, chitosan or polygalactosamine.

5. The process of claim 1 wherein the naphthoquinone derivative is 2,5,8-trihydroxy-1,4-naphthoquinone.

6. The process of claim 1 wherein the naphthoquinone derivative is 2-bromo-5,8-dihydroxy-1,4-naphthoquinone or 2-chloro-5,8-dihydroxy-1,4-naphthoquinone.

7. The process of claim 1 wherein the naphthoquinone derivative is deoxyshikonin or shikonin.

8. The process of claim 1 wherein the naphthoquinone derivative is acethylshikonin.

9. The process of claim 1 wherein the naphthoquinone derivative is β,β-dimethylacrylshikonin.

10. The process of claim 1 wherein the naphthoquinone derivative is isobutylshikonin, isovalerylshikonin or α-methyl-n-butylshikonin.

11. The process of claim 1 wherein the naphthoquinone derivative is β-hydroxyisovalerylshikonin.

12. The process of claim 1 wherein the naphthoquinone derivative is teracrylshikonin.

13. The process of claim 1 and further comprising extracting said naphthoquinone derivative from the root of Lithospermum.

14. The process of claim 3 and further comprising extracting said naphthoquinone derivative from the root of Lithospermum.

15. The process of claim 1 wherein said treating is done at a temperature in the range of from 60° C. to 90° C. and for a period of from 30 minutes to 2 hours.

16. The process of claim 3 wherein said treating is done at a temperature in the range of from 60° C. to 90° C. and for a period of from 30 minutes to 2 hours.

17. A process for producing a black coloring material comprising treating the amino groups of a sugar in a sugar-containing material with a composition comprising a compound of the formula:

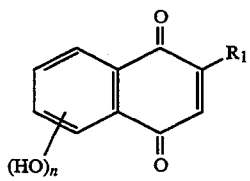

wherein R$_1$ represents a hydrogen atom, a hydroxyl group, a halogen atom, or a group represented by the following formula:

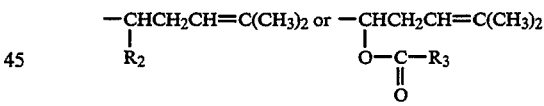

wherein R$_2$ represents a hydrogen atom or a hydroxyl group, R$_3$ represents an alkyl group, an alkenyl group or a hydroxylalkyl group, and n represents 1 or 2.

* * * * *

UNITED STATES PATENT AND TRADEMARK OFFICE
CERTIFICATE OF CORRECTION

PATENT NO. : 5,358,538
DATED      : October 25, 1994
INVENTOR(S): SUSUMU SHIMOYAMA et al.

It is certified that error appears in the above-identified patent and that said Letters Patent is hereby corrected as shown below:

Col. 2, lines 19, 22 and 25, change "spectroreflectvitity" to--spectroreflectivity--.

Col. 4, line 34, change "-1,4-naphthoquine" to---1,4-naphthoquinone--.

Col. 11, line 4, change "Lithoxpermum" to--Lithospermum--.

Col. 11, line 37, at the beginning of the line, add--(8)--.

Col. 11, line 47, change "produced" to--produce--.

Signed and Sealed this

Ninth Day of May, 1995

Attest:

BRUCE LEHMAN

*Attesting Officer*    *Commissioner of Patents and Trademarks*